United States Patent [19]

Yunker et al.

[11] Patent Number: 5,075,554

[45] Date of Patent: Dec. 24, 1991

[54] SCINTILLATION CAMERA GANTRY SUPPORTING A PLURALITY OF DETECTOR HEADS BETWEEN TWO PARALLEL PLATES

[75] Inventors: David A. Yunker, Cicero; Albrecht H. Enders, Palatine, both of Ill.

[73] Assignee: Siemens Gammasonics, Inc., Hoffman Estates, Ill.

[21] Appl. No.: 589,291

[22] Filed: Sep. 27, 1990

[51] Int. Cl.⁵ ............................................. G01T 1/166
[52] U.S. Cl. ........................ 250/363.08; 250/363.02; 250/363.04; 250/363.05; 250/394
[58] Field of Search ...................... 250/363.01, 363.02, 250/363.04, 363.05, 363.08, 363.10, 394

[56] References Cited

U.S. PATENT DOCUMENTS 4,511,801  4/1985  Tatham et al. ........................ 250/394
4,651,007  3/1987  Perusek et al. .................. 378/189 X

*Primary Examiner*—Constantine Hannaher
*Attorney, Agent, or Firm*—Mark H. Jay

[57] ABSTRACT

A gantry for a multi-head scintillation camera including a pair of vertically disposed annular plates between which are mounted the scintillation camera heads. The plates are supported on their peripheral edges by rollers which both provide load bearing support and allow plate rotation. A pulley is mounted on one of the plates and is belt-driven by a motor.

5 Claims, 2 Drawing Sheets

SCINTILLATION CAMERA GANTRY SUPPORTING A PLURALITY OF DETECTOR HEADS BETWEEN TWO PARALLEL PLATES

BACKGROUND OF THE INVENTION

This invention relates to scintillation cameras used for medical diagnosis and, more particularly, to a gantry for supporting and rotating the detectors of a multi-head scintillation camera around a patient.

In single photon emission computed tomography (SPECT) systems, a camera head rotates around the region (head, heart) to be imaged. Although such an arrangement is operative, it is wasteful, since when the head is in one angular orientation with respect to the patient, radiation at all other angles is not being collected. In addition, it takes a relatively long time to conduct a SPECT study because of the time required to get a complete data set by stepping the head completely around the patient's body.

It has therefore being proposed to rotate simultaneously a plurality of heads around the patient. This results in the collection of more data during a particular interval of time or, alternatively, reduces the time needed to collect a predetermined amount of data, thereby permitting either better images or faster throughput as required by the diagnostician. Furthermore, the newer radioisotopes currently in use have shorter half-lives, so that speed in data collection is essential, since if the data is not collected quickly it disappears.

Three-head camera SPECT units presently available include an annular plate having the three detector heads of the scintillation camera mounted thereon. The plate is attached to a gantry frame and rotates to allow data collection by all the heads at each selected angle around the imaged organ. The detector heads move radially in and out to make either a large or small central opening, depending on the patient's size and the organ being studied. A problem with this type of unit is that the heavy heads and their supports mounted on one side of the annular plate create cantilevered stresses and forces which, because they are not counterbalanced, require massive supporting structures. It is therefore a primary object of this invention to provide a multi-head scintillation camera which is statically balanced in the vertical direction and which therefore does not need a massive gantry.

SUMMARY OF THE INVENTION

The foregoing and additional objects are attained in accordance with the principles of this invention by providing a pair of parallel spaced annular plates between which the radiation detection heads making up the camera are mounted. The plates are disposed vertically and are each separately supported on their peripheral edges for rotation. Drive means is provided for rotating the plates.

. In accordance with an aspect of this invention, the plate supporting structure includes a plurality of rollers in supporting contact with the peripheral edge of each of the plates.

BRIEF DESCRIPTION OF THE DRAWINGS

The foregoing will be more readily apparent upon reading the following description in conjunction with the drawings in which like elements in different figures thereof have the same reference numeral and wherein.

DETAILED DESCRIPTION OF PREFERRED EMBODIMENTS

Figure 1:
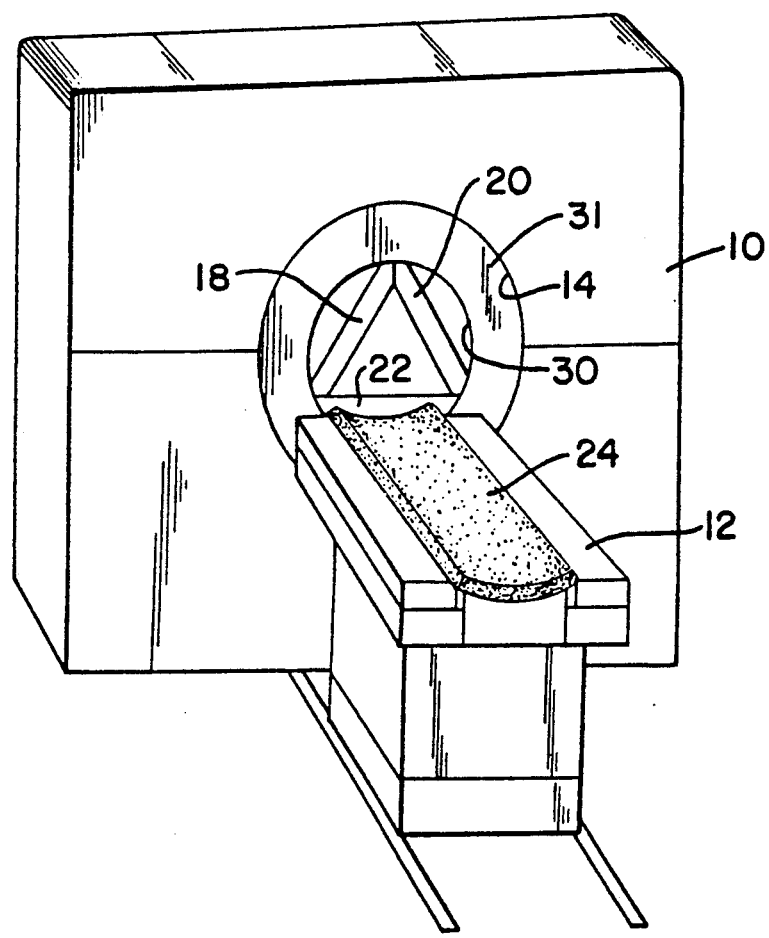
FIG. 1 is a perspective view of a patient support table and a scintillation camera housing constructed in accordance with the principles of this invention.

FIG. 1 illustrates a scintillation camera housing 10 with a patient support table 12 adjacent thereto. The housing 10 is formed with an opening 14 through which may be seen a scintillation camera gantry constructed according to this invention. As will be clear from the following discussion, the gantry includes a first plate 16, which provides partial support for a scintillation camera which includes the detector heads 18, 20 and 22. The table 12 includes a slidable patient support pallet 24 which is arranged for movement into and out of the housing 10 so that a SPECT study may be performed on the patient. In accordance with this invention, the gantry for supporting and rotating the heads 18, 20, 22 comprises the first plate 16 and the second plate 26. The plates 16 and 26 are parallel spaced apart annular plates which are located relative to each other so that a line 28 defining a main axis and extending through the centers of the plates 16 and 26 is orthogonal to both the plates 16 and 26. The plate 16 has a central opening 30 and the plate 26 has a central opening 32, each of the central openings 30, 32 being concentric with its respective plate 16, 26. The openings 30, 32 each are partially filled with an annular cover 31 and 33 respectively. Each of the covers 31 and 33 has a central opening which is sufficient to allow a patient lying on the support pallet 24 to pass therethrough.

The plates 16, 26 are connected together by a plurality of cross beams 34 which also serve as mounting brackets for the detector heads 18, 20, 22. The cross beams 34 are arranged so that the heads 18, 20, 22 are equiangularly spaced about the main axis 28. Additionally, there is mounted on the beams 34 structure for moving the heads 18, 20, 22 each along a respective straight line path radially from the main axis 28. Movement of the heads 18, 20, 22 is controlled by a computer (not shown) in accordance with the requirements of the study specified by the diagnostician. In some studies, this movement is simultaneous and at the same rate so that the heads 18, 20, 22 are equidistant from the main axis 28; where this is so, the gantry is inherently balanced in the rotational direction. In others, it is desired that the heads 18, 20, 22 be positioned as closely as possible to the patient and that they move e.g. closer to and further away from the main axis 28 to follow the body contours of the patient. In these latter studies, movement of the heads 18, 20, 22 is carried out independently and rotational balance of the gantry is inherently lacking.

Figure 3:
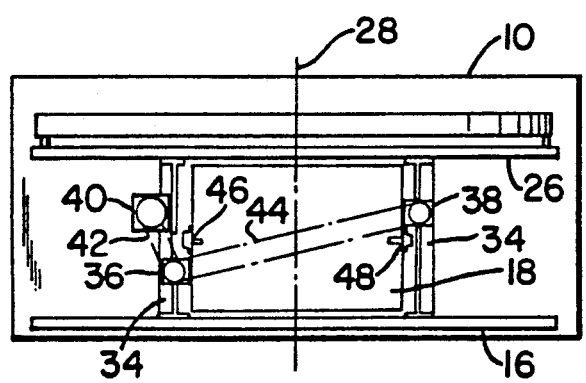
FIG. 3 is a plan view of the gantry of FIG. 2, shown with only one camera for purposes of simplification.
Figure 4:
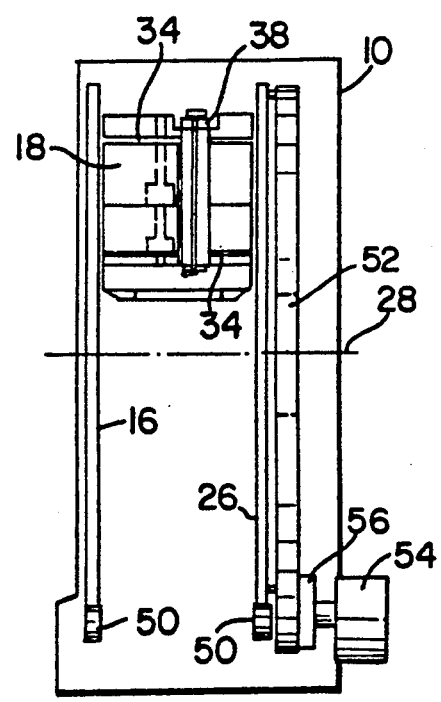
FIG. 4 is a side view of the gantry of FIGS. 2 and 3, shown with only one head for purposes of simplification.

Such moving structure illustratively includes for each of the heads a pair of acme screw drives 36, 38 driven by a motor 40 through belts 42, 44. To provide further support for the heads 18, 20, 22, there is provided for each of the heads a pair of linear bearings 46, 48. As is most clearly shown in FIG. 3, the screw drive 36 is on the same side of head 18 as is the linear bearing 46 and the screw drive 38 is on the same side of the head 18 as is the linear bearing 48. The screw drives 36, 38 are offset and the linear bearings 46, 48 are aligned with each other so as to provide a four point support for the head 18 and prevent it from cocking when being driven. Thus, a line joining the screw drives 36, 38 intersects a line joining the linear bearings 46, 48 at substantially the center of the head 18 so that all forces are balanced. Advantageously although not necessarily, one of the bearings (e.g. bearing 48) uses ball bearings and the other (e.g. bearing 46) uses cam followers or rollers. This structure is presently preferred because the use of two identical sets of linear bearings of the ball bearing type would require adherence to stricter tolerances and would therefore increase manufacturing costs. Where one linear bearing is of the cam follower type, slight dimensional variances can be accommodated without requiring tighter tolerances.

Figure 2:
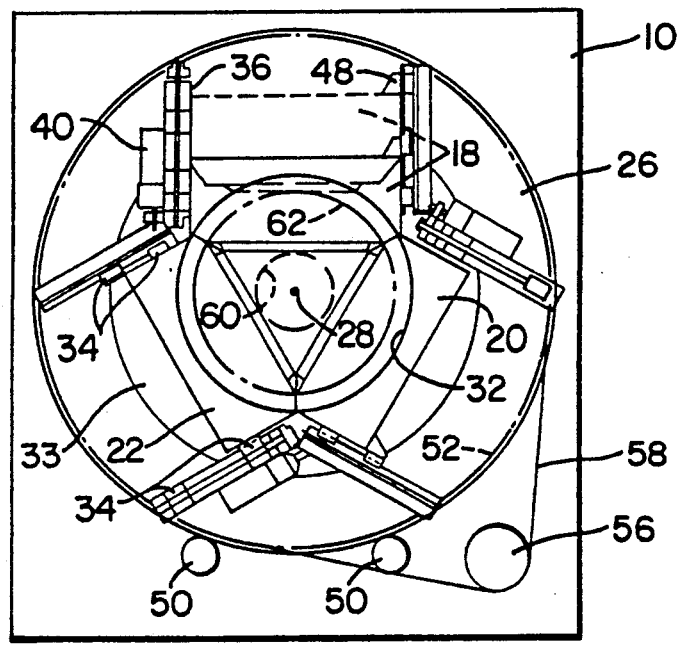
FIG. 2 is an elevational view schematically depicting a gantry according to this invention as viewed with one of the plates removed.

To provide support for the gantry and allow rotation, there is provided a plurality of support rollers 50, illustratively four in number. The rollers 50 support the plates 16, 26 in a vertical orientation by being in supporting contact with the peripheral edges of the plates 16, 26. There are two support rollers 50 for each of the plates 16, 26, the support rollers 50 for each of the plates 16, 26 being equiangularly disposed on opposite sides of a vertical line passing through the axis 28, as is best seen in FIG. 2. The rollers 50 are each mounted for rotation about a respective axis parallel to the main axis 28 so that in addition to providing load bearing vertical support for the plates 16, 26, they also allow rotation of the plates 16, 26. Such rotation is accomplished by providing a drive pulley 52 mounted to the plate 26, the drive pulley 52 having its axis co-linear with the main axis 28. A motor 54 is provided having its output shaft coupled (via a speed-reducing gearbox, not shown) to an output pulley 56 and a belt 58 couples the pulleys 56 and 52 so that the motor 54 can effect rotation of the plates 16, 26, resulting in rotation of the heads 18, 20, 22 about the main axis 28. The gearbox is provided because rotational imbalances may be substantial and substantial torque may be required to rotate the gantry.

Rotation of the plates 16, 26 and radial movement of the heads 18, 20, 22 are under control of a computer (not shown). As shown in FIG. 2 for the head 18, each of the heads may be moved radially from an innermost position shown in solid lines to an outermost position shown in broken lines. At the innermost position, the central portion of the heads provides a minimum orbit 60 of approximately 25 centimeters and at the outermost position the maximum orbit 62 is approximately 60 centimeters. The size of the orbit depends upon the size of the patient and the organ being imaged, cranial imaging requiring a smaller diameter orbit than heart imaging.

Accordingly, there has been disclosed an improved gantry for supporting and rotating a multi-head scintillation camera around a patient. By providing a pair of vertically disposed plates supporting the heads therebetween, with vertical support for the plates, the system is statically balanced and a massive support structure is unnecessary. While a single embodiment has been disclosed, it will be apparent to those of ordinary skill in the art that various modifications and adaptations to the disclosed arrangement are possible, and it is only intended that this invention be limited by the scope of the appended claims. Thus, while three heads have been illustrated, systems having two or more heads may be constructed according to this invention.

We claim:

1. A gantry for a multi-head radiation detection camera comprising:

a pair of parallel spaced apart annular plates, said plates being located relative to each other so that a line defining a main axis and extending through the centers of said plates is orthogonal to both said plates, each of said plates having a central opening concentric with the respective plate, said opening being large enough to accommodate a patient's body;

means for mounting a plurality of radiation detection heads between and to said plates, said mounting means including means for moving each of said detection heads along a respective straight line path which extends radially with respect to said main axis, said mounting means being arranged so that said detection heads are spaced equiangularly about said main axis and are limited to motion along said straight line paths;

means for supporting each of said plates in a substantially vertical plane, said supporting means allowing rotation of said plates about said main axis and including a plurality of rollers each mounted for rotation about a respective axis parallel to said main axis, a first group of said plurality of rollers being in supporting contact with the peripheral edge of a first of said plates and the remainder of said plurality of rollers being in supporting contact with the peripheral edge of the other of said plates; and drive means for rotating said plates about said main axis.

2. The gantry of claim 1 wherein there are four rollers with each of said plates being supported by two rollers which are disposed on opposite sides of a vertical line passing through said main axis.

3. The gantry of claim 1 wherein said drive means includes:

a drive pulley mounted to one of said plates for movement therewith, the axis of said drive pulley being co-linear with said main axis;

an output pulley mounted for rotation about an axis parallel to said main axis; motor means coupled to drive said output pulley; and a belt coupling said output pulley to said drive pulley.

4. The gantry of claim 1 wherein said moving means includes for each of said detection heads:

a pair of screw drives each mounted to a respective one of a pair of opposite sides of said each detection head;

a pair of linear bearings each mounted to a respective one of said pair of opposite sides of said each detection head; and motor means for simultaneously driving said screw drives;

wherein said screw drives and said linear bearings are all parallel to said radial straight line path.

5. The gantry of claim 4 wherein said screw drives and said linear bearings are so situated on said pair of opposite sides that a line joining said pair of screw drives intersects a line joining said pair of linear bearings at substantially the center of said each detection head.

* * * * *